US012674128B2

(12) United States Patent
Wang et al.

(10) Patent No.: US 12,674,128 B2
(45) Date of Patent: Jul. 7, 2026

(54) MEMBRANE AND METHOD FOR CULTURE AND DIFFERENTIATION OF CELLS

(71) Applicant: OUJIANG LABORATORY, Wenzhou (CN)

(72) Inventors: Pengyuan Wang, Wenzhou (CN); Chang Cui, Wenzhou (CN); Jiaxian Wang, Wenzhou (CN)

(73) Assignee: OUJIANG LABORATORY, Wenzhou (CN)

( * ) Notice: Subject to any disclaimer, the term of this patent is extended or adjusted under 35 U.S.C. 154(b) by 1148 days.

(21) Appl. No.: 17/696,904

(22) Filed: Mar. 17, 2022

(65) Prior Publication Data

US 2022/0275319 A1     Sep. 1, 2022

Related U.S. Application Data

(63) Continuation of application No. 16/429,042, filed on Jun. 2, 2019, now abandoned.

(51) Int. Cl.
| | |
|---|---|
| *C12N 5/077* | (2010.01) |
| *C12M 1/12* | (2006.01) |
| *C12N 5/0735* | (2010.01) |
| *C12N 5/074* | (2010.01) |
| *C12N 5/0775* | (2010.01) |
| *B82Y 30/00* | (2011.01) |

(52) U.S. Cl.
CPC ........... *C12M 25/02* (2013.01); *C12N 5/0606* (2013.01); *C12N 5/0657* (2013.01); *C12N 5/0663* (2013.01); *C12N 5/0667* (2013.01); *C12N 5/0696* (2013.01); *B82Y 30/00* (2013.01); *C12N 2533/10* (2013.01); *C12N 2533/30* (2013.01); *C12N 2533/70* (2013.01); *C12N 2535/00* (2013.01); *C12N 2537/00* (2013.01); *C12N 2539/00* (2013.01)

(58) Field of Classification Search
None
See application file for complete search history.

(56) References Cited

PUBLICATIONS

Cui et al. "Binary Colloidal Crystals Drive Spheroid Formation and Accelerate Maturation of Human-Induced Pluripotent Stem Cell-Derived Cardiomyocytes" (2019), Applied Materials & Interfaces, vol. 11: 3679-3689. (Year: 2019).*
Wang et al. Binary colloidal crystals (BCCs) as a feeder-free system to generate human induced pluripotent stem cells (hiPSCs). (2016), Scientific Reports, vol. 6: 36845, pp. 1-11 (Year: 2016).*
Wang et al. "Topographical Modulation of Pluripotency and Differentiation of Human Embryonic Stem Cells" (2018), IEEE Transaction on Nanotechnology, vol. 17, No. 3: 381-384 (Year: 2018).*
Beers et al. "Passaging and colony expansion of human pluripotent stem cells by enzyme-free dissociation in chemically defined culture conditions" (2012), Nat Protoc, 7(11): 2029-2040. (Year: 2012).*

* cited by examiner

*Primary Examiner* — Teresa E Knight

(57) ABSTRACT

Provided is a membrane for cell culture and differentiation. The membrane comprises a base portion and an array of protrusions consisting of a plurality of protrusions. The protrusions are substantially evenly distributed on the base portion. The plurality of protrusions has dimensions on the order of micrometers. In particular, the membrane consists of particles of different particle sizes of two or more types. One type of particles has an average particle size of 1 μm to 50 μm. Two or more types of particles of different particle sizes include nanoscale particles, 10-900 nm. One type of particle is selected from the group consisting of inorganic compound microspheres. The other type of particles of the two or more types of particles of different particle sizes is selected from the group consisting of organic polymer nanospheres. Also provided is a method for maintaining, culturing and/or differentiating cells using such membrane.

15 Claims, 13 Drawing Sheets

Monolayer Binary Colloidal Crystals (BCCs)

MEMBRANE AND METHOD FOR CULTURE AND DIFFERENTIATION OF CELLS

CROSS-REFERENCE TO RELATED APPLICATIONS

This application is a U.S. continuation of co-pending U.S. application Ser. No. 16/429,042, filed on Jun. 2, 2019, the disclosure of which is incorporated herein by reference in their entireties.

TECHNICAL FIELD

The present disclosure relates to the technical field of cell culture and cell differentiation. In particular, the present disclosure relates to the field of cell differentiation using a multi-scale particle membrane. More particularly, the present disclosure relates to a one-step method for expansion of human induced pluripotent stem cells (hiPSCs) and directed differentiation of hiPSCs into mature cardiomyocytes using the multi-scale particle composited membrane.

BACKGROUND ART

In recent years, stem cell-based research has made rapid progress, making it possible to cure heart-related diseases. Human induced pluripotent stem cells (iPSCs) belong to pluripotent stem cells that can differentiate into functional cardiomyocytes in vitro, which may be used for repairing a heart. Since iPSCs can be derived from autologous cells, there are no issues such as ethics and immunosuppression. Since direct transplantation of iPSCs has a high risk of tumorigenesis, it is a better treatment means to first differentiate iPSCs into cardiomyocytes in vitro before transplantation. iPSC-CMs are cardiomyocytes (CMs) obtained by inducing directed differentiation of iPSCs, and are the best cell type for the construction of disease models in vitro, drug screening and cell transplantation treatment. Studies have shown that in mouse and porcine myocardial infarction models, iPSC-CMs can survive in a heart of a host and improve cardiac functions after transplantation. hiPSC-CMs exhibit many characteristics that are the same as the characteristics of normal cardiomyocytes in vivo, such as morphological structure, gene expression, functional ion channels, receptor expression, and electrophysiological properties. These characteristics make hiPSC-CMs a good model for drug cardiotoxicity testing in vitro. At present, the obstacle to improving the efficiency of new drug research and development is that in vitro cardiomyocytes are not mature enough, which makes it impossible to accurately predict drug toxicity. High yield and high maturities are the prerequisites and key for the reliable application of hiPSC-CMs in drug screening in vitro.

Current methods for inducing differentiation of hiPSCs into hiPSC-CMs include (1) 3D induction method based on embryoid bodies (EBs) and (2) 2D induction method of single cell seeding.

The 3D induction method based on EBs is to first culture the hiPSC suspension to form EBs, and then inoculate the EBs on feeder cells or extracellular matrix (for example, Matrigel) for adherent culture, which finally obtains, by virtue of the interaction between cells in the EBs and the factors in the culture medium, the hiPSC-CMs with spontaneous contraction and rhythmic beats. This method involves two steps and has low differentiation efficiency, and in this method cells within the EBs are highly different. For these shortcomings, the 2D induction method of single cell has recently been widely utilized.

In the 2D induction method, cells are directly contacted with soluble biochemical factors in a medium to cause rapid differentiation of the cells. Initially, in the 2D induction method, mouse visceral endoderm-like cells (END-2) were used as feeder cells to produce Activin-A and BMP factors to promote the formation of ventricular-like cardiomyocytes. Recently, the addition of biochemical factors or chemical small molecules has increased the controllability of intracellular signaling pathways, which has become the main means of myocardial differentiation. A "matrix sandwich" method using Matrigel combined with growth factors Activin-A/BMP4/FGF2 can also increase cardiomyocyte production. In clinical use, the above conventional method is still subject to certain restrictions, involving, for example, cells and products derived from animals, heterogeneity of hiPSC-CMs (incompletely differentiated or undifferentiated cells are present in the cell population), and relatively low degree of maturation of cells in the case of adherent culture on a traditional substrate in a 2D manner. Thus, currently it is still the main problem to get high-purity and high-maturity hiPSC-CMs.

In summary, the prior art for stimulating the differentiation of hiPSCs into hiPSC-CMs has the following disadvantages.

1) In the traditional 3D method based on EBs, it is necessary to first prepare EBs, and then transfer EBs from suspension culture to adherent culture, which is time consuming and inefficient.

2) The traditional 2D method is to culture hiPSCs using a two-dimensional planar surface and obtain hiPSC-CMs by adding small molecule compounds or growth factors, which may result in low cell maturity due to failure to meet bionic requirements.

3) Since layered iPSC-CMs are obtained by the traditional 2D method, a digestive enzyme should be used to remove the cells from the surface in the later stage, which may cause damage and quantity loss to the cells.

SUMMARY

The present disclosure provides a membrane for culture and differentiation of cells, comprising:

(A) a base portion; and (B) a protrusion array composed of a plurality of protrusions substantially distributed on the base portion, the plurality of protrusions having a size on the order of micrometers.

The present disclosure also provides a method of culture and/or differentiation of cells, comprising culturing and/or differentiating the cells on the membrane of the present disclosure.

The present disclosure also provides a method for maintaining growth and stemness of cells, comprising culturing cells on the membrane of the present disclosure, wherein the cells are selected from the group consisting of induced pluripotent stem cells, embryonic stem cells, or adult stem cells.

BRIEF DESCRIPTION OF DRAWINGS

In order to more clearly illustrate embodiments of the present disclosure or technical solutions in the prior art, drawings to be used in the description of embodiments or the prior art are briefly described below.

In FIG. 3, A represents larger particles, and B represents smaller particles distributed between the larger particles.

As shown in FIG. 4, four days before the start of cell differentiation, hiPSCs were expanded on Matrigel-coated 4 BCC surfaces and coverslip surfaces (as control), and then maintained on a mTeSR medium.

When hiPSCs reached 80% confluence, a cell differentiation step is started, and the medium was changed to RPMI1640 (Gibco, 1744361) with B-27 (Gibco, A1895601). The cells were also exposed to the GSK3-β inhibitor CHIR 99021 (6 μM, Selleck, S2924) at the beginning of differentiation, followed by a Wnt antagonist IWR-1 (5 μM, Sigma-Aldrich, 10161). Contracting cells were noted from day 8 and were fed every alternate day with RPMI1640 supplemented with the B-27 supplement (Gibco, 17504-044). During day 15-20, the medium was changed to a purification medium, which consists of a glucose-free Dulbecco's modified Eagle's medium (Gibco, 11966025) supplemented with 4 mM lactic acid and sterile 1M Na-4-(2-hydroxyethyl)-1-piperazineethanesulfonic acid (HEPES). After 30 days of in vitro differentiation, the cells were trypsinized and replated on gelatin-coated coverslips (Solarbio, YA0352) for further experiments.

Figure 5A:
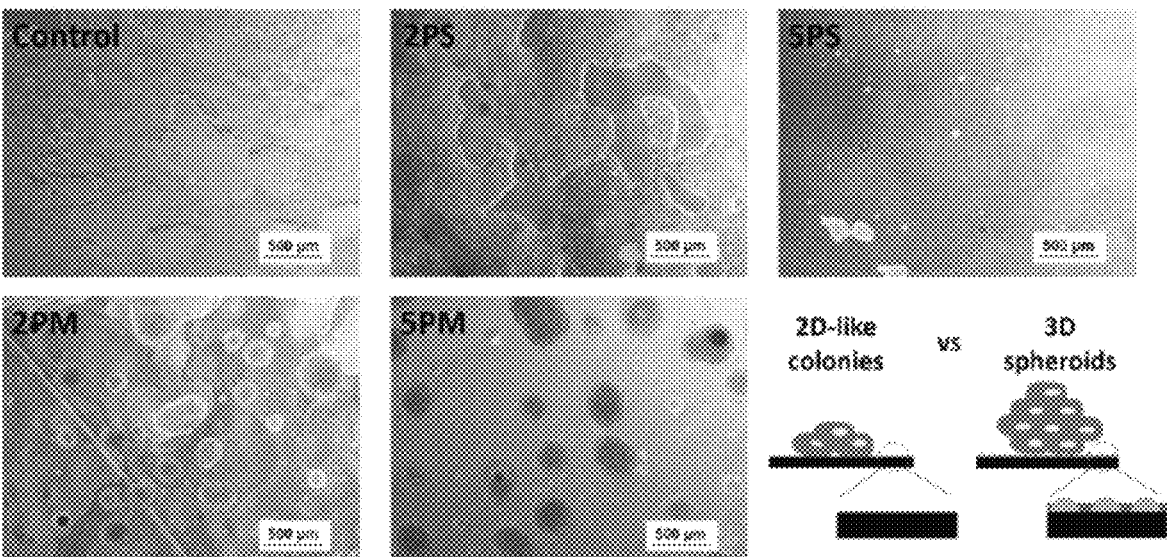

FIG. 5A is a schematic diagram showing the morphology of the hiPSCs observed under a microscope on day 2 from the start of differentiation on different surfaces (scale bar 500 μm), and a comparison of a 2D-like cell population grown on the smooth control substrate with the 3D cell spheroids grown on the BCCs.

Figure 5B:
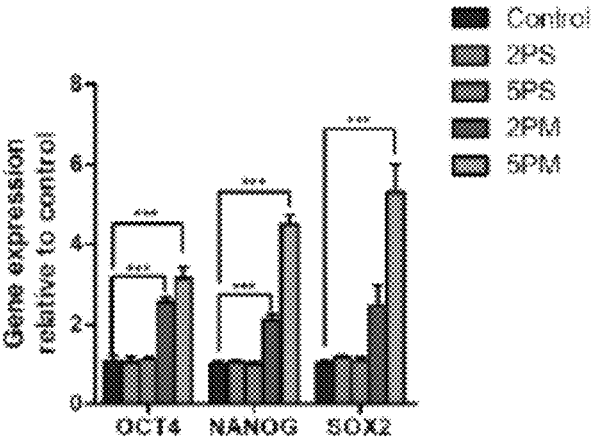

FIG. 5B shows the expression of three stemness-related genes OCT4, NANOG and SOX2 in hiPSCs grown on 2PS, 5PS, 2PM and 5PM of the present disclosure, relative to those in hiPSCs grown on control substrates, on day 2 from the start of differentiation.

Figure 6A:
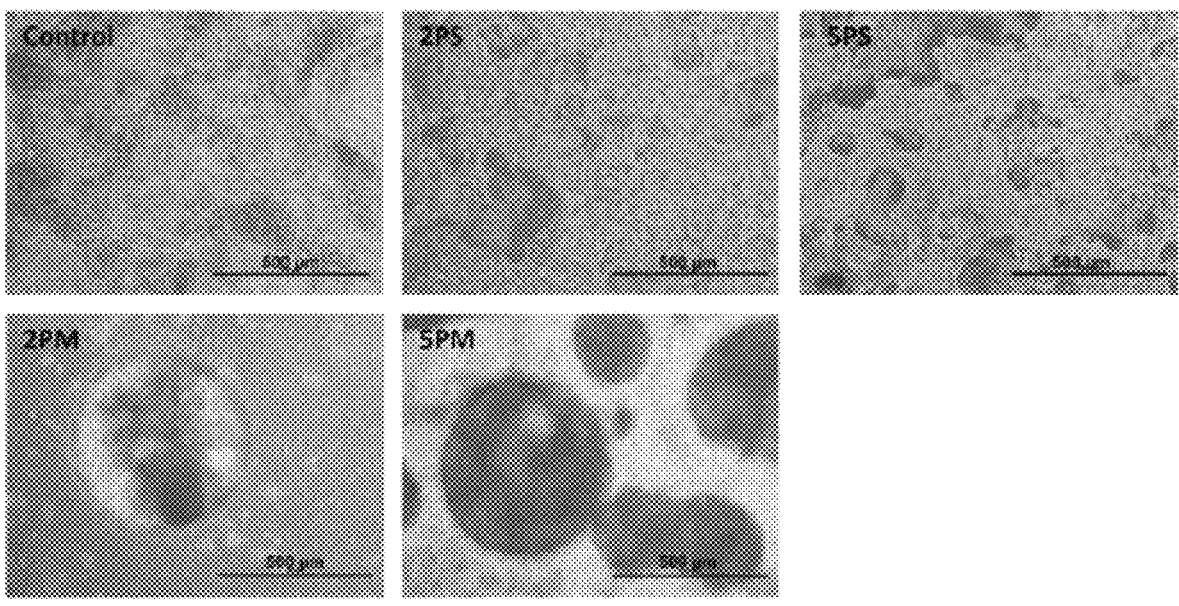

FIG. 6A shows the morphology of the hiPSCs (scale bar 500 μm) observed under a microscope on day 8 from the start of the differentiation.

Figure 6B:
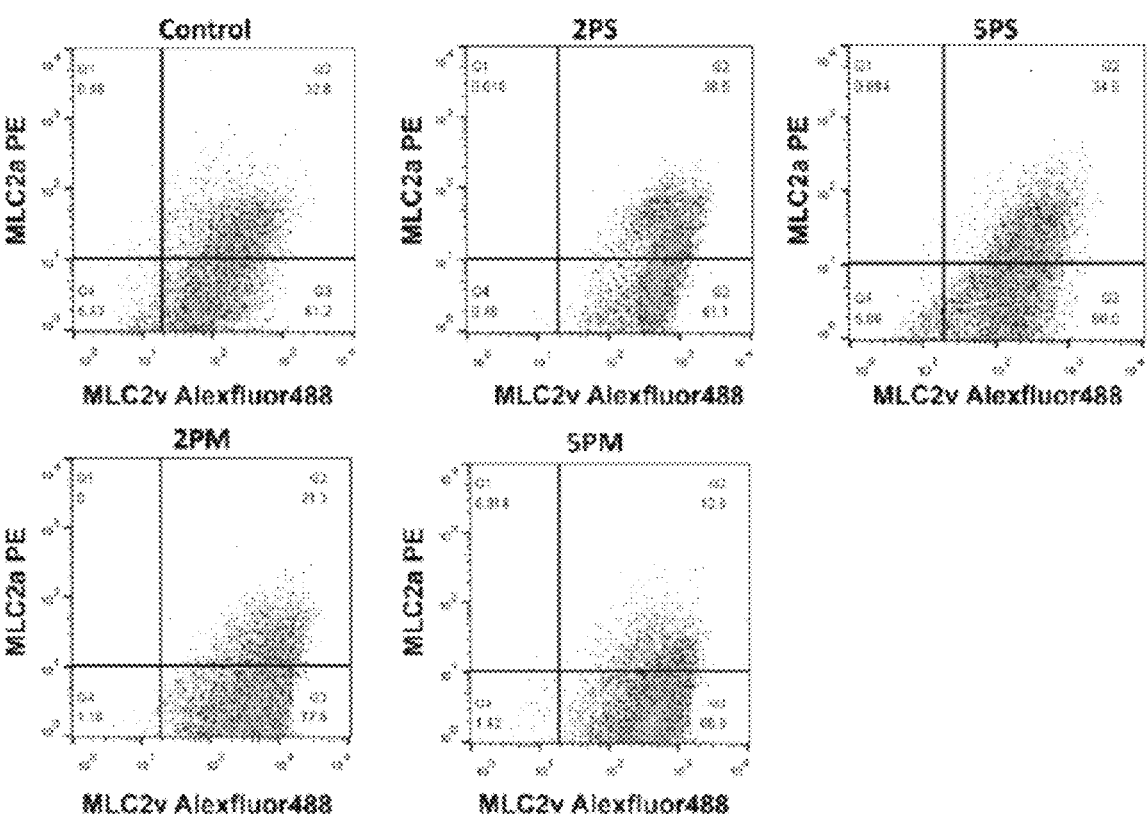

FIG. 6B shows cell type analysis (flow cytometry) of MLC2v and MLC2a. The cells show two types of fluorescence, MLC2v and MLC2a.

Figure 6C:
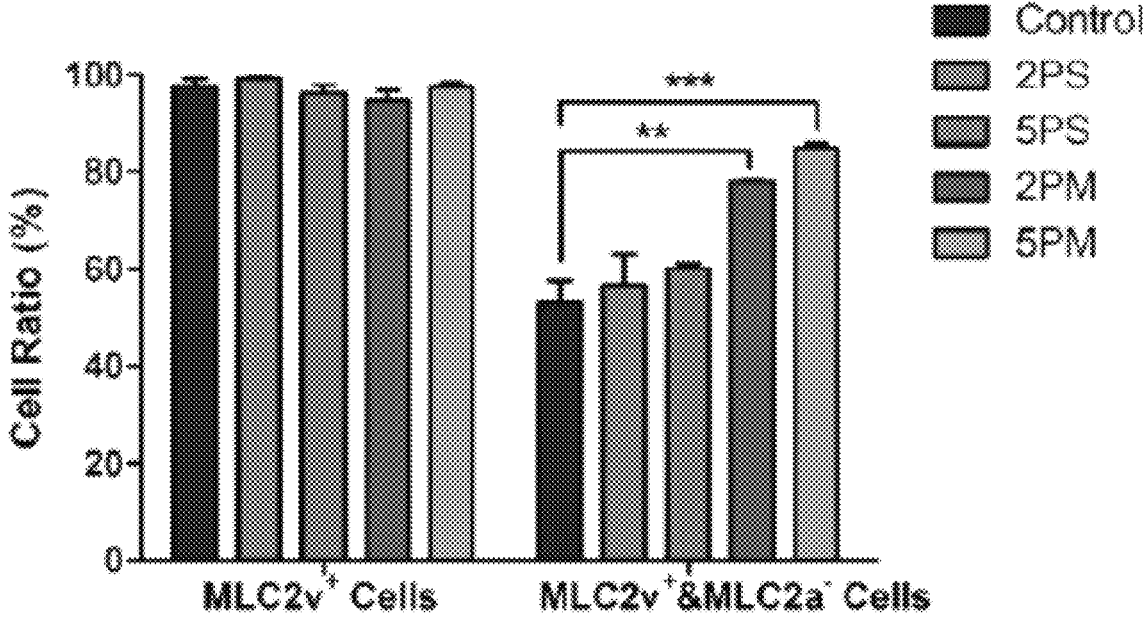

FIG. 6C shows ratios of MLC2v+ cells and ratios of MLC2v+/MLC2a− cells (a mature ventricular cardiomyocyte subtype) (n=3), in mean±SD.p≤0.005, *p≤0.001, estimated by one-way ANOVA analysis, followed by Dunnet test.

Figure 7A:
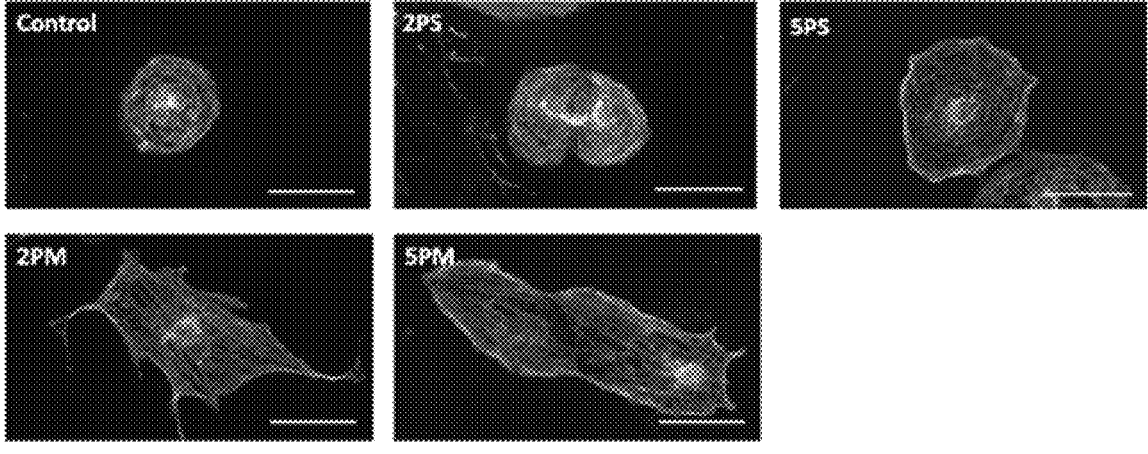

FIG. 7A shows α-actinin, α-tubulin and DAPI staining of a single hiPSC-CM on day 30 from the start of the differentiation (scale bar=50 μm).

Figure 7B:
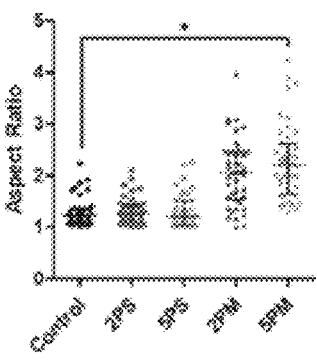

FIG. 7B shows aspect ratios of hiPSC-CMs (n=40-44, median (interquartile range), estimated by Nemenyi test).

Figure 7C:
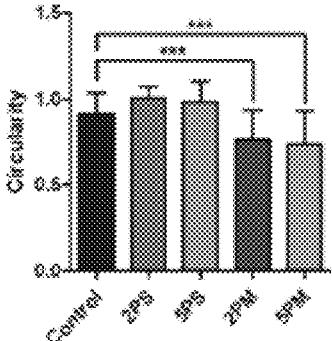

FIG. 7C shows circularity of hiPSC-CMs (n=40-44, estimated by one-way ANOVA analysis followed by Dunnet test).

Figure 7D:
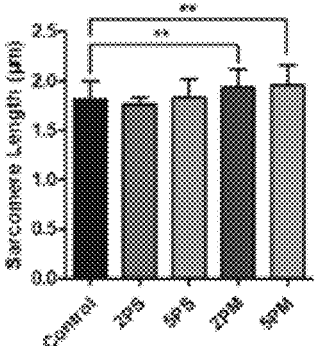

FIG. 7D shows the length of the sarcomere (n=40-44, estimated by one-way ANOVA analysis followed by Dunnet test).

Figure 8:
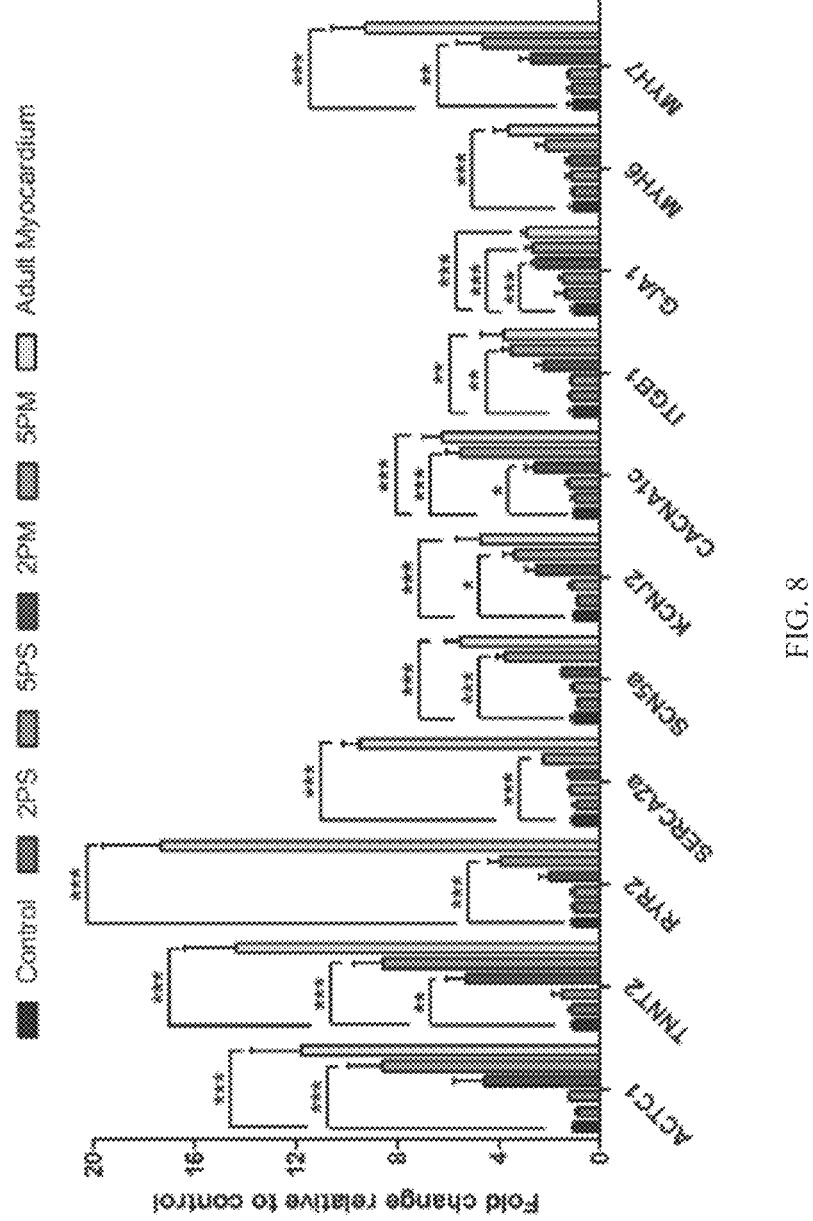

FIG. 8 shows expressions of essential cardiac genes ACTC1, TNNT2, RYR2, SERCA2a, SCN5a, KCNJ2, CACNA1c, ITGB1, GJA1, MYH6 and MYH7 on day 30 from the start of the differentiation.

Figure 9A:
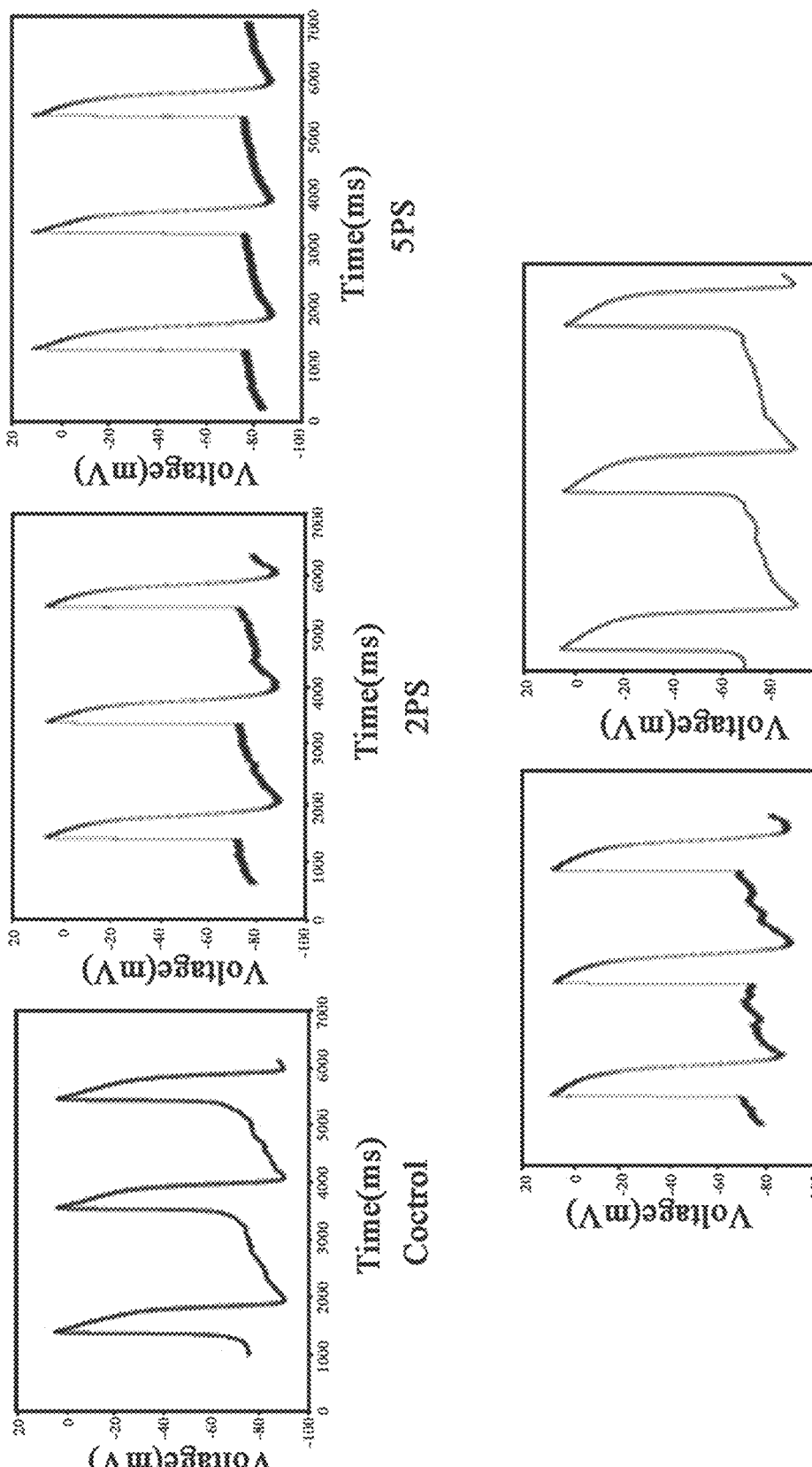

FIG. 9A shows the action potential (AP) of hiPSC-CMs on day 30 from the start of the differentiation.

Figure 9B:
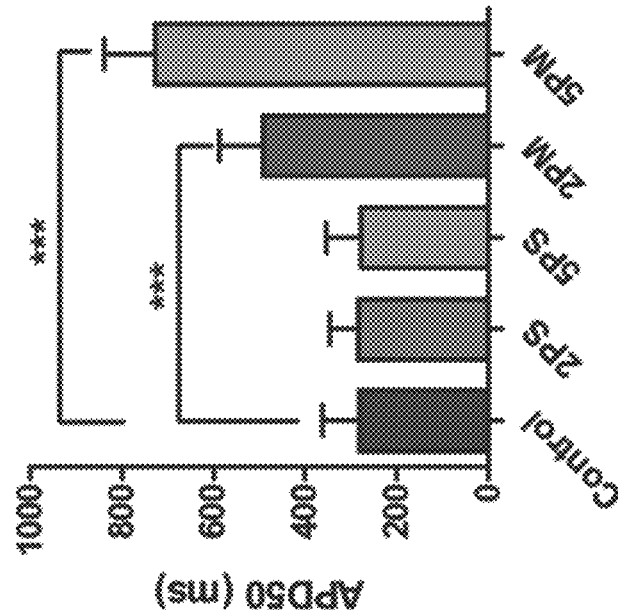
Figure 9C:
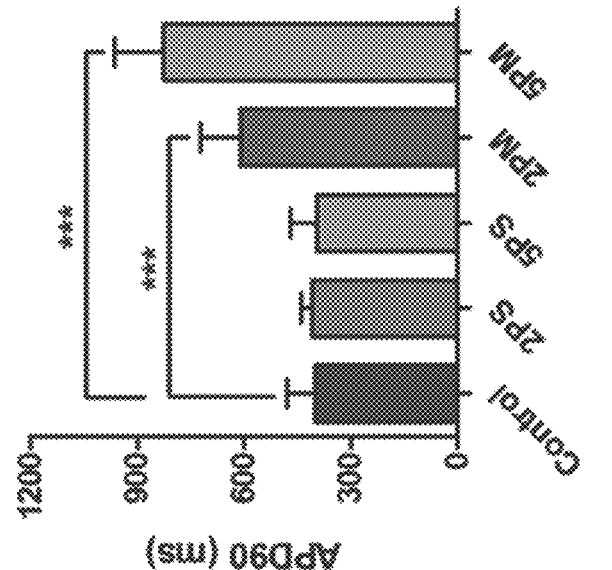

FIGS. 9B and 9C show AP duration at 50 and 90% repolarization, APD50 and APD90, respectively.

Figure 9D:
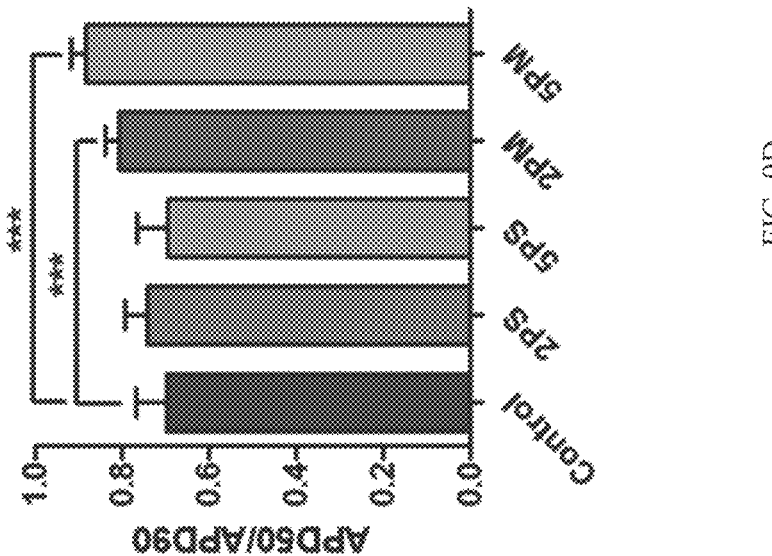

FIG. 9D shows a ratio of APD50/APD90 (n=10).

Figure 10A:
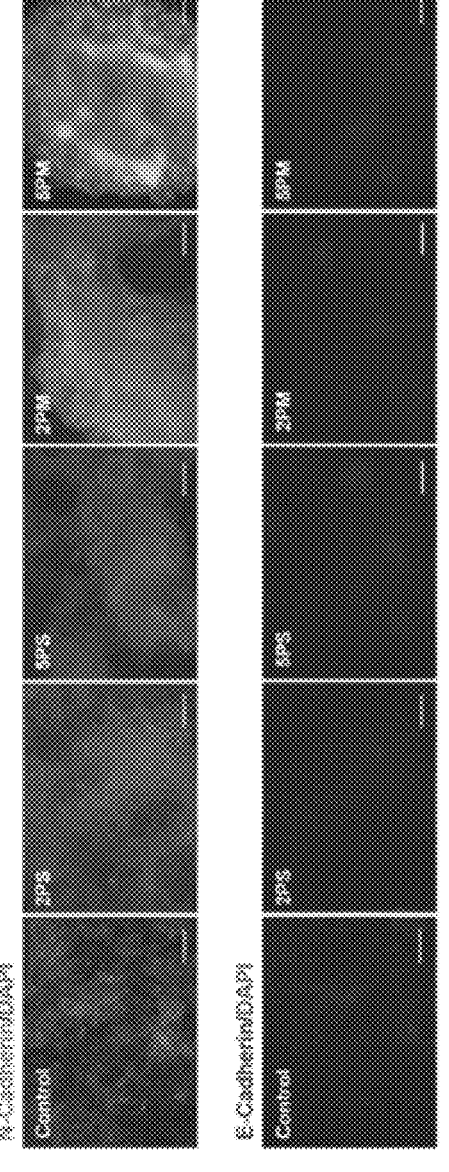

FIG. 10A shows staining of N-cadherin, E-cadherin, and DAPI from hiPSC-CMs on five surfaces on day 30 from the start of the differentiation.

Figure 10B:
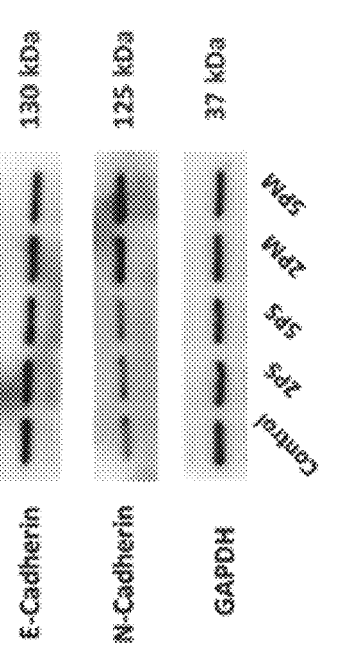
Figure 10C:
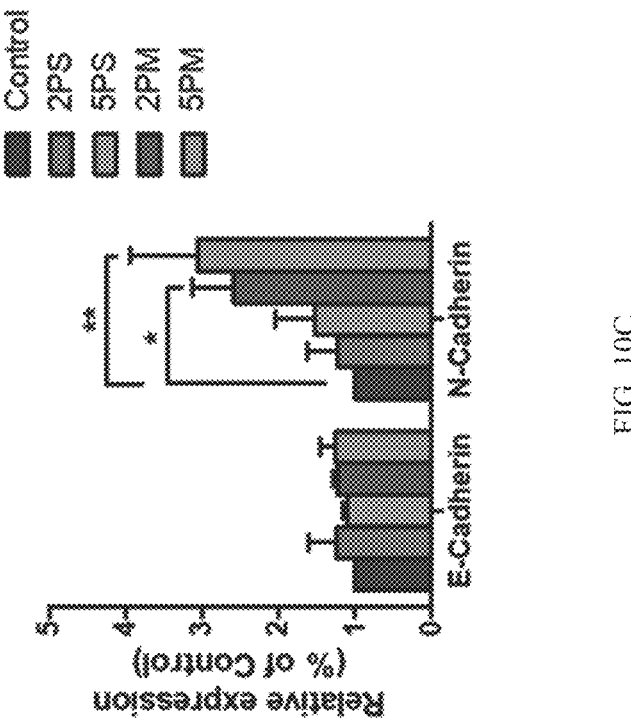

FIGS. 10B and 10C show Western blot analysis of E-cadherin and N-cadherin of the five groups (n=3, estimated by one-way ANOVA analysis followed by Dunnet test).

DETAILED DESCRIPTION OF EMBODIMENTS

Unless defined otherwise, all technical and scientific terms used herein have their common meaning as understood by one of ordinary skill in the art to which this invention is related.

Before describing the present invention in detail, it is to be understood that this invention is not limited to specific compositions or process steps, as such can vary. As used in this specification and the appended claims, the singular forms "a", "an" and "the" include plural referents unless the context clearly dictates otherwise. The terms "a" (or "an"), as well as the terms "one or more," and "at least one" can be used interchangeably herein.

It is understood that wherever embodiments are described herein with language "comprising", otherwise analogous embodiments described in terms of "consisting of" and/or "consisting essentially of" are also provided.

As used herein, the term "multi-scale particle membrane" or "membrane", when used in culture, growth or differentiation of cells, refers to a substrate for culture, growth or differentiation of cells. The term "multi-scale particle membrane" or "membrane" includes two-scale particle membrane, three-scale particle membrane, four-scale particle membrane, and the like. The term "multi-scale particle membrane" or "membrane" includes a monovalent particle membrane, a binary particle membrane, a ternary particle membrane, a quaternary particle membrane, and the like. The "multi-scale particle membrane" or "membrane" is preferably a BCC membrane with different particle sizes.

The term "colloidal crystal" is a two-dimensional or three-dimensional ordered array structure that is formed by assembly of monodisperse micrometer-, submicrometer- or nanometer-sized inorganic or organic particles (also called colloidal particles) via gravity, electrostatic force or capillary force, similar to a crystal with an atom or molecule as a standard repeating unit. One example of a colloidal crystal in the disclosure is a colloidal crystal composed of micrometer-sized silica and nanometer-sized poly(methyl methacrylate).

The term "cell" is herein used in its broadest sense in the art and refers to a living body which is a structural unit of tissue of a multicellular organism, is surrounded by a membrane structure which isolates it from the outside, has the capability of self-renew, and has genetic information and a mechanism for expressing it. Cells used herein may be naturally-occurring cells or artificially modified cells (e.g., fusion cells, genetically modified cells, etc.).

As used herein, the term "stem cell" refers to a cell being capable of self-renew and having pluripotency. Typically, stem cells can regenerate injured tissue. Stem cells herein may be, but are not limited to, embryonic stem (ES) cells or tissue stem cells (also called tissue-specific stem cells, or somatic stem cells). Any artificially produced cell which can have the above-described abilities may be a stem cell.

"Embryonic stem (ES) cells" used herein are pluripotency stem cells derived from early embryos. An ES cell was first established in 1981, which has also been applied to the production of knockout mice since 1989. In 1998, a human ES cell was established, which is currently becoming available for regenerative medicine.

The term "pluripotency" as used herein refers to the ability of a cell to differentiate into cells derived from any of the three germ layers: endoderm (e.g., interior stomach lining, gastrointestinal tract, the lungs), mesoderm (e.g., muscle, bone, blood, urogenital system), or ectoderm (e.g., epidermal tissues and nervous system). "Pluripotent stem cells" used herein refer to cells that can differentiate into cells derived from any of the three germ layers.

The term "induced pluripotent stem cells" or "iPSCs" refers to a type of pluripotent stem cells artificially prepared from non-pluripotent cells. Cardiomyocytes derived from iPSCs are a useful experimental system that has great potential. They offer innovative human preparation for cardiac repair, drug safety design and testing, clinical diagnosis, and research. Cardiomyocytes derived from iPSCs offer the opportunity to work on cells that recapitulate the activity of healthy human cardiomyocytes, which are otherwise rarely available for comprehensive experimental investigation. Human iPSC (hiPSC)-derived cardiomyocytes offer the ability to develop predictive tools for cardiac function.

As used herein, "differentiation" refers to a change that occurs in cells to cause those cells to assume certain specialized functions and to lose the ability to change into certain other specialized functional units. Cells capable of differentiation may be any of totipotent, pluripotent or unipotent cells. For mature adult cells, differentiation may be partial or complete.

"Differentiated cell" refers to a non-embryonic cell that is present in a particular differentiated, i.e., non-embryonic, state. The three earliest differentiated cell types are endoderm, mesoderm, and ectoderm. The hiPSC-CM as described herein is a cardiomyocyte obtained by inducing differentiation of pluripotent stem cells.

The present disclosure provides a membrane for culture and differentiation of cells, comprising:

(A) a base portion; and (B) a protrusion array composed of a plurality of protrusions substantially uniformly distributed on the base portion, the plurality of protrusions having a size on the order of micrometers.

In one or more embodiments, a distance between adjacent protrusions is on the order of micrometers. The distance between the adjacent protrusions is a distance between the centers of the adjacent protrusions. In particular, when the protrusions are particles or microspheres, the distance between adjacent protrusions is a distance between the centers of adjacent particles or a distance between the centers of adjacent microspheres.

In one or more embodiments, the base portion and/or the plurality of protrusions are made of a biocompatible material.

In one or more embodiments, the membrane is a colloidal crystal membrane.

In one or more embodiments, the protrusions are formed by particles.

In one or more embodiments, the membrane is composed of particles of different particle sizes of two or more types, wherein the two or more types of particles of different particle sizes comprise at least:

the first type of particles serving as the protrusions and having an average particle size of from 1 μm to 50 μm, and the second type of particles serving as the base portion and having an average particle size less than or equal to ½ of that of the first type of particles.

In one or more embodiments, the two or more types of particles of different particle sizes comprise the first type of particles serving as the protrusions and having an average particle size of 1 μm to 10 μm; and the second type of particles serving as the base portion and having an average particle size less than or equal to ½ of that of the first type of particles.

In one or more embodiments, the protrusions or the particles of the first type have an average particle size of 1-40 μm, 1-30 μm, 1-20 μm, 1-10 μm, 1-9 μm, 1-8 μm, 1-7 μm, 1-6 μm, 1-5 μm, 1.5-5 μm, 2-5 μm or 2.5-4 μm. The particles of the first type have an average particle size of 1 μm, 2 μm, 3 μm, 4 μm, 5 μm, 6 μm, 7 μm, 8 μm, 9 μm, 10 μm or 11 μm.

In one or more embodiments, the particles of the second type have an average particle size less than or equal to ½, ⅓, ¼, ⅕, ⅙, ⅐, ⅛, ⅑, $\frac{1}{10}$, $\frac{1}{11}$, $\frac{1}{12}$, $\frac{1}{13}$, $\frac{1}{14}$, $\frac{1}{15}$, $\frac{1}{16}$, $\frac{1}{17}$, $\frac{1}{18}$, $\frac{1}{19}$, $\frac{1}{20}$, $\frac{1}{21}$, $\frac{1}{22}$, $\frac{1}{23}$, $\frac{1}{24}$, $\frac{1}{25}$, $\frac{1}{26}$, $\frac{1}{27}$, $\frac{1}{28}$, $\frac{1}{29}$, $\frac{1}{30}$, $\frac{1}{40}$, $\frac{1}{50}$, $\frac{1}{60}$, $\frac{1}{70}$, $\frac{1}{80}$, $\frac{1}{90}$, $\frac{1}{100}$, $\frac{1}{150}$, $\frac{1}{200}$, $\frac{1}{250}$, $\frac{1}{300}$, $\frac{1}{350}$, $\frac{1}{400}$, $\frac{1}{450}$ or $\frac{1}{500}$ of the average particle size of the first type of particles.

In one or more embodiments, the particles of the second type have an average particle size of 10-900 nm, 20-800 nm, 30-700 nm, 40-750 nm, 50-700 nm, 60-650 nm, 70-600 nm, 80-500 nm, 95-400 nm, 100-400 nm, 120-380 nm, 140-360 nm, 160-340 nm, 180-320 nm, 200-300 nm or 220-280 nm. In one or more embodiments, the particles of the second type have an average particle size of 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 450 nm, 500 nm, or 600 nm.

In one or more embodiments, the membrane is composed of particles of different particle sizes of two types, wherein in the particles of different particle sizes of the two types, particles of a first type have an average particle size of 1 μm to 50 μm, and particles of a second type are nano-sized or have an average particle size of 10 nm to 900 nm. The protrusions or the particles of the first type have an average particle size of 1-40 μm, 1-30 μm, 1-20 μm, 1-10 μm, 1-9 μm, 1-8 μm, 1-7 μm, 1-6 μm, 1-5 μm, 1.5-5 μm, 2-5 μm or 2.5-4 μm. The protrusions or the particles of the first type have an average particle size of 1 μm, 2 μm, 3 μm, 4 μm, 5 μm, 6 μm, 7 μm, 8 μm, 9 μm, 10 μm or 11 μm. The particles of the second type have an average particle size of 10-900 nm, 20-800 nm, 30-700 nm, 40-750 nm, 50-700 nm, 60-650 nm, 70-600 nm, 80-500 nm, 95-400 nm, 100-400 nm, 120-380 nm, 140-360 nm, 160-340 nm, 180-320 nm, 200-300 nm or 220-280 nm. The particles of the second type have an average particle size of 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 450 nm, 500 nm, or 600 nm.

Without being limited by theory, it is believed that a membrane composed of particles with different sizes of two or more types, when serving as a substrate, is advantageous to stemness maintenance and differentiation of cells thereon, producing different effects depending on the proportions and combinations. Since two or more types of particles can have different effects on cell adhesion, for example, some cells prefer to adhere to small particles rather than large particles, it is made possible to regulate the adhesion degree of cells to the surface of the particle membrane, so as to promote cell-cell interactions, facilitating the cells' forming 3D-like spheroids thereon. Such a 3D-like morphology thus facilitates the maintenance of stemness and pluripotency of stem cells in a culture medium. In addition, the formation of such 3D-like spheroid of cells on the membrane of the present disclosure also allows the culture, differentiation and harvest of cells to be performed in one step on the membrane of the present disclosure, without any necessity to perform the steps of first forming EBs and then transferring cells, or the step of using digestive enzymes after two-dimensional differentiation. Meanwhile, the membrane of the present disclosure also allows differentiated cells formed thereon to have higher maturity than differentiated cells obtained on a conventional substrate, which is embodied in the function of cardiomyocytes.

In one or more embodiments, the protrusions or the particles of the first type and/or the particles of the second type are monodisperse particles.

In one or more embodiments, the protrusions or the particles of the first type are made of an inorganic compound.

In one or more embodiments, the array of protrusions is made of a single material, such as $SiO_2$, or of multiple materials, such as a combination of $TiO_2$ and $SiO_2$.

In one or more embodiments, the particles of the second type having a diameter of 10-900 nm are distributed in the array of protrusions. The particles of the second type may be made of a single material, such as polystyrene (PS) or a mixture of different materials, such as a mixture of PS and PMMA particles.

In one or more embodiments, the base portion or the particles of the second type are made of an organic polymer, preferably a polymeric nanosphere.

In one or more embodiments, the protrusions or the particles of the first type are made of one or more materials selected from the group consisting of silica, titania, zinc oxide, chemically modified silica, chemically modified titanium dioxide, chemically modified zinc oxide, and any combination thereof.

In one or more embodiments, the base portion or the particles of the second type is/are made of one or more materials selected from the group consisting of polystyrene, acrylic polymer, chitosan, poly(lactic-co-glycolic acid) (PLGA), polylactic acid, polycaprolactone, gelatin and any combination thereof.

In one or more embodiments, the acrylic polymer is selected from the group consisting of poly(meth)acrylic acid, poly(meth)acrylate, and any combination thereof.

In one or more embodiments, the poly(meth)acrylate is selected from the group consisting of poly(methyl)acrylic acid $C_1$-$C_{20}$ alkyl esters.

In one or more embodiments, the poly(meth)acrylate is selected from the group consisting of poly(methyl acrylate), poly(methyl methacrylate), poly(ethyl acrylate), poly(ethyl methacrylate), poly(propyl acrylate), poly(propyl methacrylate), poly(butyl acrylate), poly(butyl methacrylate), poly(pentyl acrylate), poly(pentyl methacrylate), poly(hexyl acrylate), poly(hexyl methacrylate) and any combination thereof.

In one or more embodiments, the protrusions or the particles of the first type are made of silica, preferably silica microspheres, and the base portion or the particles of the second type are made of poly(methyl methacrylate), preferably poly(methyl methacrylate) nanospheres.

Without being limited by theory, it is believed that the combination of inorganic compound microspheres and organic polymer nanospheres may chemically improve the interaction between the cells and membrane surface, further facilitating the formation of 3D-like spheroids on the membrane of the present disclosure. Therefore, a suitable combination of inorganic compound microspheres and organic polymer nanospheres facilitates maintenance of cell stemness of the stem cells, increases the efficiency of cell differentiation, and improves the maturity of differentiated cells. The use of an organic polymer as the particles of the second type or relatively small particles in certain embodiments is also advantageous in that it can be thermally dissolved or partially dissolved with an organic solvent, so as to fix the membrane. In some embodiments, the inorganic particles serving as the particles of the first type (protrusions) or relatively large particles are also advantageous in that they have high density and thus are easier to precipitate, facilitating the preparation of the membrane.

In one or more embodiments, the particles of the first type are present as a single layer of particles, and the ratio of the particles of the first type to the particles of the second type is determined such that the particles of the first type are distributed in the particles of the second type in a partially embedded manner. For example, in the case where the particles of the first type or relatively large particles in the membrane are arranged in a single layer, 1 cm2 area requires about 2 µl of a 2 µm particle suspension (10%), or 5 µL of a 5 µm particle suspension (10%). In some embodiments, the amount of relatively small particles or the particles of the second type serving as filler materials is determined in such a calculation manner that a height of half of the diameter of the relatively large particles is reached. For example, 1.5 µl of a suspension of a second type of 400 nm particles or relatively small particles is used for a membrane of the first type of 5 µm particles or relatively large particles. Because there will be losses in the process, the above amount is only an estimated value, and the dose in actual product may be higher.

The present disclosure also provides a method for culture and/or differentiation of cells, comprising culturing and/or differentiating the cells on the membrane of the present disclosure.

In one or more embodiments, the method of culturing cells comprises:

(1) inoculating the cells onto the membrane of the present disclosure, and (2) culturing the cells.

In one or more embodiments, the method of differentiating the cells comprises:

(1) implanting the cultured cells onto the membrane of the present disclosure, and (3) inducing differentiation of the cells.

In one or more embodiments, the method for culturing and/or differentiating cells comprises:

(1) inoculating the cells onto the membrane of the present disclosure, (2) culturing the cells in a first medium, and (3) inducing differentiation of the cells in a second medium, wherein the step of culturing the cells and the step of inducing differentiation of the cells are both performed on the membrane.

The steps of culture and differentiation of the cells in the methods of the present disclosure are both performed on the membrane of the present disclosure, that is, the method of the present disclosure does not require the cells to form into EBs first, for example, by suspension culture, and then transferred to a culture vessel or scaffold for an adherent culture so as to achieve differentiation. Therefore, the method of the present disclosure is time and effort saving, and also avoids cell damage or quantity loss caused by the transfer process, achieving efficient cell culture and differentiation in one step.

Moreover, the differentiated cells obtained by the method of the present disclosure have a higher degree of maturity than those obtained by conventional methods.

In one or more embodiments, the cells are selected from the group consisting of induced pluripotent stem cells, embryonic stem cells, or adult stem cells.

In one or more embodiments, the cells are human induced pluripotent stem cells.

In one or more embodiments, the cells are selected from the group consisting of bone marrow mesenchymal stem cells, hematopoietic stem cells, neural stem cells, peripheral blood stem cells, adipose stem cells, placental stem cells, placental sub-totipotent stem cells, and amniotic stem cells.

In one or more embodiments, the first medium is selected from the group consisting of DMEM, DMEM/F12, RPMI-1640, mTeSR mediums, and any combination thereof.

In one or more embodiments, the second medium is selected from the group consisting of DMEM medium supplemented with B-27, DMEM/F12 medium supplemented with B-27, RPMI-1640 medium supplemented with B-27, mTeSR medium supplemented with B-27 and any combination thereof.

In one or more embodiments, the step of inducing differentiation of the cells further comprises exposing the cells to a GSK3-β inhibitor and/or to a Wnt antagonist.

In one or more embodiments, the cells are induced pluripotent stem cells. By the method of the present disclosure, the induced pluripotent stem cells are differentiated in a directed differentiation manner into human induced pluripotent stem cell-derived cardiomyocytes.

In one or more embodiments, the membrane is pre-coated with Matrigel.

In one or more embodiments, the method further comprises separating the cells from the membrane by flushing or suction after the step of inducing differentiation of the cells. For example, about 8 days after the start of directed myocardial differentiation, after forming spherical aggregates, the cells can be separated from the membrane by suction or flushing.

In one or more embodiments, the flushing is performed with a buffer or a culture medium.

The prior art 2D cell culture and differentiation method require the use of an enzyme (e.g., trypsase) for digestion after the completion of the culture and differentiation in order to separate the cells from a substrate, which, however, will cause damages to the cells and complicate the culture and differentiation process. For the method of the present disclosure, the cells obtained by culture and differentiation can be separated from the membrane by simple means, such as flushing and suction, thus avoiding cell damage and loss in quantity, thereby maximally protecting the cells and simplifying the process.

In one or more embodiments, the membrane is prepared by the following steps, (a) providing a dispersion of the particles of the first type in a first dispersion medium, (b) providing a dispersion of the particles of the second type in a second dispersion medium, (c) distributing the two dispersions on a base material, and (d) removing the first dispersion medium and the second dispersion medium such that the particles of the first type are distributed on the base material in a single layer and partially embedded in the particles of the second type.

The membrane of the present disclosure is simple in preparation, and a plurality of membranes of the present disclosure can be prepared in a short time, thereby simplifying the process of cell culture and differentiation using the membrane of the present disclosure.

In one or more embodiments, the first dispersion medium and the second dispersion medium are water.

In one or more embodiments, the first dispersion medium and the second dispersion medium are removed by evaporation.

The present disclosure provides a method for maintaining growth and stemness of cells, comprising culturing the cells on the membrane as described in the present disclosure.

In one or more embodiments, the cells are selected from the group consisting of induced pluripotent stem cells, embryonic stem cells and adult stem cells.

In one or more embodiments, the method for maintaining growth and stemness of cells comprises (a) inoculating the cells onto the membrane according to the present disclosure, and (b) maintaining the cells in a first medium.

In one or more embodiments, the cells are selected from the group consisting of induced pluripotent stem cells, embryonic stem cells and adult stem cells.

EXAMPLES

The embodiments of the present disclosure will be described in detail below with reference to examples, but those skilled in the art will understand that the following examples are only intended to illustrate the present disclosure, and should not be construed as limiting the scope of the present disclosure. Examples are carried out according to the conventional conditions or the conditions recommended by the manufacturer, if specific conditions are not described. All reagents or instruments used, whose manufacturers are not indicated, are commercially available conventional products.

Example 1

Preparation of BCC Membrane

The multifunctional particle membrane of this example is composed of two types of different particles, wherein the large particles are inorganic silica particles, and the small particles are organic polymer particles. 2SiPM (also referred to as 2PM herein) consists of 2 μm silica microspheres (SiO₂) and 0.1 μm poly(methyl methacrylate) (PMMA) nanoparticles, 5SiPM (also referred to as 5PM herein) consists of 5 μm SiO₂ microspheres and 0.2 μm PMMA nanoparticles, 2SiPS (also referred to as 2PS herein) consists of 2 μm SiO₂ microspheres and 0.2 μm polystyrene (PS) nanoparticles, and 5SiPS (also referred to as 5PS herein) consists of 5 μm SiO₂ microspheres and 0.4 μm PS nanoparticles.

Figure 1:
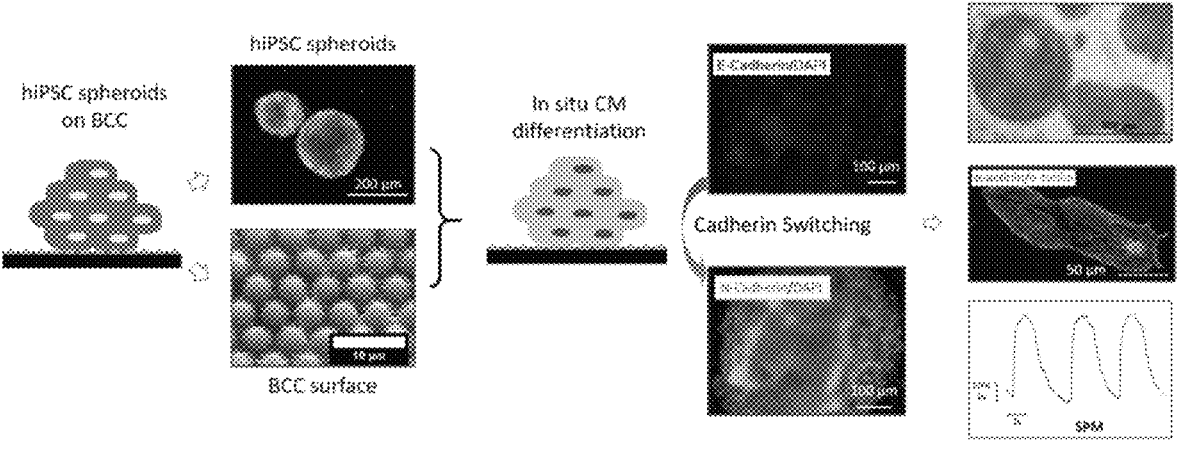
FIG. 1 generally illustrates a process of an embodiment of the present disclosure, including a one-step process of inducing directed differentiation of hiPSCs into hiPSC-CMs on a multi-scale particle membrane, and functional identification of the resultant hiPSC-CMs.
Figure 2:
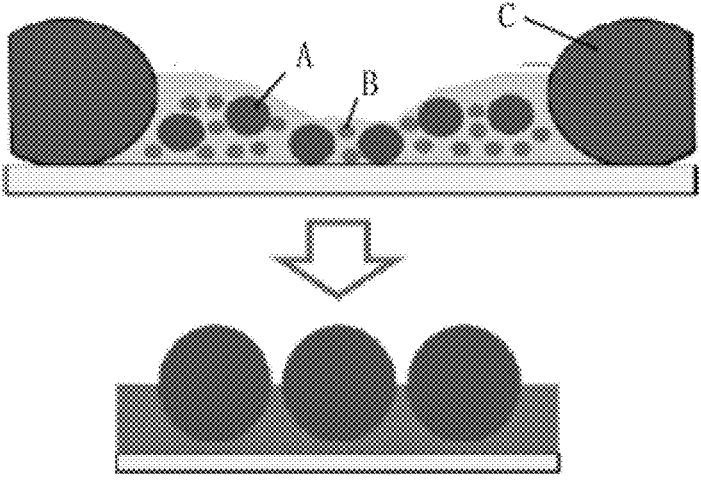
FIG. 2 shows a schematic diagram of precipitation-based self-assembly of a single layer binary colloidal crystal (BCC) membrane as an example of a multi-scale particle membrane, wherein A represents large-sized particles, B represents small-sized particles, and C represents an O-ring.

The preparation process comprises the following steps. Two types of particles of different sizes were separately dispersed in water to obtain colloidal solutions, and the two colloidal solutions are mixed well, wherein the mixing volumes of the two types of particles are calculated in such a manner that the particles can form a single-layer membrane on a surface of a coverslip. Then, the mixture was added dropwise to a coverslip (Solarbio, YA0352), water was evaporated to self-assemble the particles on the surface of the coverslip to form a multi-stage structure (see FIG. 2), and finally the surface of the multi-stage structure was stabilized by heating. Sterilization is performed by UV irradiation before use.

Figure 3:
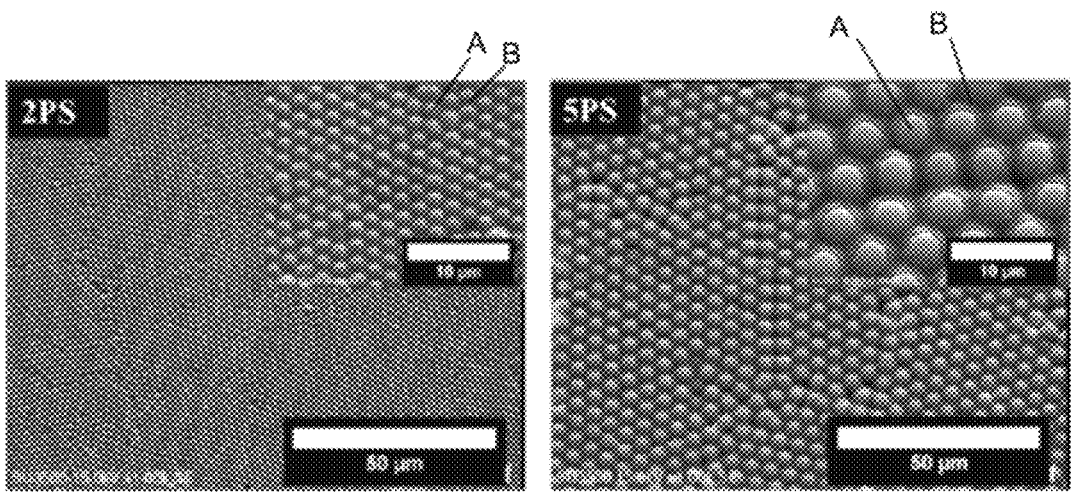
FIG. 3 shows the surface SEM images of four binary colloidal crystal (BCC) membranes 2PS, 5PS, 2PM and 5PM as examples of multi-scale particle membranes, wherein 2PS is composed of 2 μm silicon dioxide (SiO2) microspheres and 0.2 μm polystyrene (PS) nanoparticles, 5PS is composed of 5 μm SiO2 microspheres and 0.4 μm PS nanoparticles, 2PM is composed of 2 μm silica microspheres and 0.1 μm poly(methyl methacrylate) (PMMA) nanoparticles, and 5PM is composed of 5 μm SiO2 microspheres and 0.2 μm PMMA nanoparticles.
Figure 3:
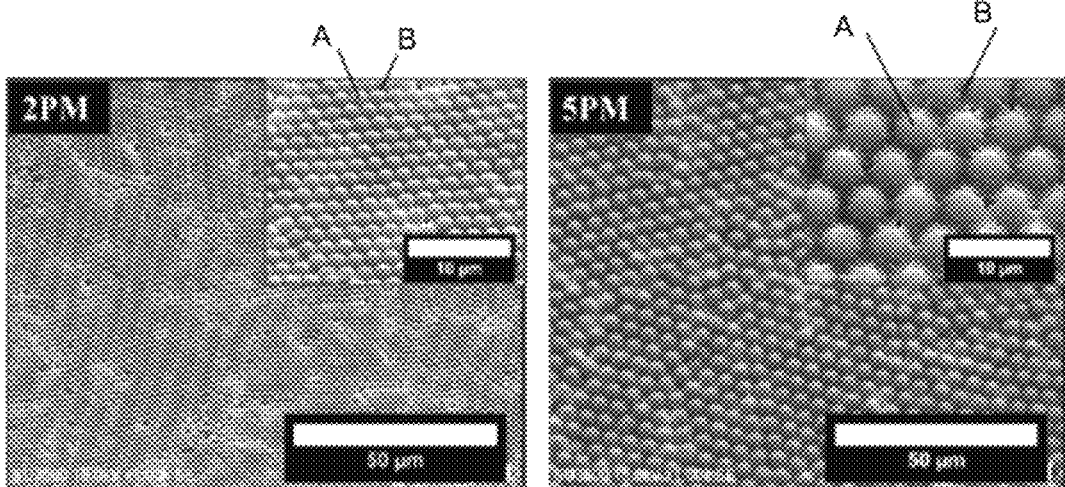

The surface structure of the four materials was characterized by scanning electron microscopy, with the detailed structure shown in FIG. 3. It can be seen that the large particle component (silica) is spread on the surface of the coverslip in a single layer and partially embedded in the small particle component (organic polymer). Thus, a surface composed of a single-layer dispersed micrometer-sized (2 or 5 μm) large particles and nano-sized (100 or 400 nm) small particles is formed. The sizes and combinations of the two types of particles are advantageous for cell differentiation.

Example 2 hiPSC Cell Culture

Four BCCs membranes and a control coverslip were coated with Matrigel (Corning, 354277). The hiPSC cell line NC5 (Help Stem Cell Innovations, NC2001) was inoculated onto the coated surface and expanded, and the seeding density was 1×106/10 cm2. The cells were maintained in a mTeSR medium (Stemcell, 05850) with 5% CO2 and at 37° C.

Cardiac Differentiation of hiPSC

Directed cardiac differentiation of hiPSCs involves the following steps. When hiPSCs reached 80% confluence, cardiac differentiation of hiPSCs was started, and the medium was changed to RPMI1640 (Gibco, 1744361) with B-27 (Gibco, A1895601). For the early stages of differentiation, the cells were exposed to the GSK3-β inhibitor CHIR 99021 (6 μM, Selleck, S2924) followed by the Wnt antagonist IWR-1 (5 μM, Sigma-Aldrich, 10161). Contracting cells were noted from day 8 and were fed every alternate day with RPMI1640 medium (Gibco, 17504-044) supplemented with the B-27 supplement. During day 15-20, the medium was changed to a purification medium, which consists of a glucose-free Dulbecco's modified Eagle's medium (Gibco, 11966025) supplemented with 4 mM lactic acid and sterile 1M Na-4-(2-hydroxyethyl)-1-piperazineethanesulfonic acid (HEPES). After 30 days of in vitro differentiation, the cells were trypsinized and replated on gelatin-coated coverslips (Solarbio, YA0352) for further experiments.

Figure 4:
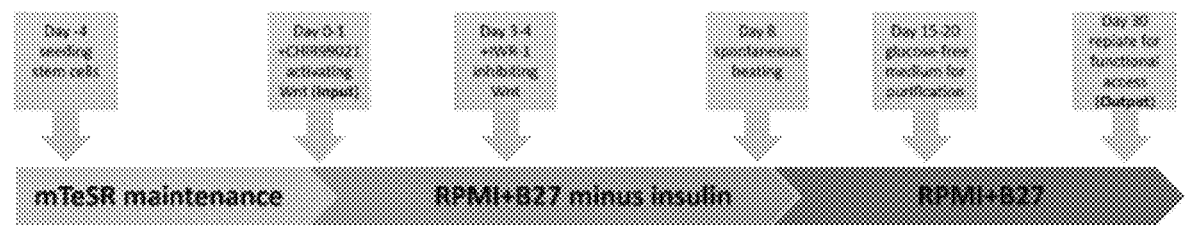
FIG. 4 shows a flow chart of the culture and differentiation of hiPSCs.

See FIG. 4 for the process of cell culture and differentiation of hiPSCs.

It should be noted that the steps of trypsinizing the differentiated hiPSC cells and replating the same on gelatin-coated coverslips in this example serve for the subsequent analysis of hiPSC-CM cells. In the production process of the hiPSC-CM cells with the purpose of preparation, the enzymolysis step is not required, instead, cell spheroids can be separated from the BCC substrate directly by flushing with, for example, buffer or medium. That is, the method in the present example does not require the steps of first suspension-culturing cells into EBs and then inoculating the same onto a substrate in the 2D induced differentiation method in the prior art.

Unlike the 3D induced differentiation method in the prior art, the method in this example does not require the steps of suspension-culturing the hiPSCs in advance to generate EBs and then implanting the same on the substrate, but the cell culture and differentiation steps of the hiPSCs are always performed on the surface of the BCC.

Example 3

Analytical Method

Immunofluorescence Staining

Cells were fixed with 4% paraformaldehyde (PFA) in Dulbecco's phosphate-buffered saline for 20 min at room temperature, and permeabilized with 0.1% Triton-X 100 for 10 min. The cells were then incubated with the following primary antibodies overnight at 4° C.: rabbit anti-Oct4 (CST, 2750S) and mouse anti-SSEA-4 (R&D, MAB1435) for pluripotency staining of hiPSCs; rabbit anti-α-tubulin (abcam, ab18251) and mouse anti-α-actinin (Sigma, A7811) for structural staining of hiPSC-CMs; and rabbit anti-N-Cadherin (abcam, ab76057) and mouse anti-E-Cadherin (abcam, ab1416) for cell adhesion staining. The secondary antibodies were donkey antirabbit IgG (Alexa Fluor 488, abcam, ab150073) and goat antimouse IgG (Alexa Fluor 555, abcam, ab150118). Nuclei were visualized with DAPI (Beyotime, C1006). Images were captured using a Zeiss fluorescence microscope (Zeiss, Axio Vert A1). Measurements of the cardiomyocyte size were performed with ImageJ software (National Institutes of Health, 1.8.0_77) [1]. The aspect ratio was defined as long axes/short axes. The circularity index was defined as $4\pi$ area/perimeter².

Flow Cytometry

Signal cardiomyocytes were obtained with trypsin and fixed in 4% PFA for 20 min. To analysis intracellular proteins, the cells were permeabilized with 0.1% Triton-X 100 for 10 min. The following primary antibodies were applied: rat anti-SSEA3 (Alexa Fluor 488, R&D, FAB1434G), rabbit anti-cardiac troponin I (Alexa Fluor 488, abcam, ab196384), rabbit anti-MYL7 (PE, Miltenyi, 130-117-546), and mouse anti-MYL2 (Alexa Fluor 488, Novus, NBP1-30249G). The stained cells were counted using BD FACS Calibur. Data analysis was performed using FlowJo software [2, 3].

Patch Clamp Assay

Whole-cell patch clamp was used to record the APs (action potentials) on the Axopatch 200B amplifier (Axon), comprising the following steps and conditions. AP was examined using the following intracellular solutions: 120 mM K-aspartate, 25 mM KCl, 5 mM Mg₂ATP, 1.8 mM CaCl₂, 5 mM HEPES, 10 mM ethylene glycolbis(β-aminoethyl ether)-N,N,N',N'-tetraacetic acid, and 10 mM glucose (pH 7.3). The composition of external Tyrode's solution was as follows: 140 mM NaCl, 5.4 mM KCl, 1 mM MgCl₂, 1.8 mM CaCl₂, 10 mM glucose, and 10 mM HEPES (pH 7.3).

For the specific procedure of the patch clamp method, please refer to Nunes, S. S.; Miklas, J. W.; Liu, J.; Aschar-Sobbi, R.; Xiao, Y.; Zhang, B.; Jiang, J.; Massé, S.; Gagliardi, M.; Hsieh, A.; Thavandiran, N.; Laflamme, M. A.; Nanthakumar, K.; Gross, G. J.; Backx, P. H.; Keller, G.; Radisic, M. Biowire: a platform for maturation of humanpluripotent stem cell-derived cardiomyocytes. Nat. Methods 2013, 10, 781-787.

Quantitative RT-PCR

RNA was isolated with Trizol (Invitrogen) following manufacturer's instructions. cDNA was produced using the iScript cDNA Synthesis Kit (170-8891, Bio-Rad). Real-time PCR was conducted using the SYBR green PCR kit (170-8882AP, Bio-Rad) and performed on a 7900HT Real-Time PCR System (Life Technologies). All PCRs were in quadruplicate and normalized to $\beta$-actin or GAPDH which were considered as the housekeeping genes. Study procedures were approved by the Bioethics Committee of the First Affiliated Hospital of Nanjing Medical University (2014-SR-090). Human adult heart tissues collected during the surgical procedures were snap-frozen in liquid nitrogen, followed by protein analysis and quantitative real-time PCR (qRT-PCR).

Western Blot

The primary antibodies used in the present study were as follows: GAPDH (1:1000, Cell Signaling, 2118S), N-cadherin (1:1000, abcam, ab76057), E-cadherin (1:1000, abcam, ab1416), cardiac troponin I (cTnI; 1:1000, abcam, ab47003), and ssTnI (1:1000, Abcam, ab8293). Secondary antibodies employed in this assay included the anti-rabbit IgG antibody (1:5000, Cell Signaling, 7074P2) or anti-mouse IgG antibody (1:5000, Cell Signaling, 7076). For the detailed procedure of Western blotting detection of N-Cadherin, please refer to Cui, C.; Geng, L.; Shi, J.; Zhu, Y.; Yang, G.; Wang, Z.; Wang, J.; Chen, M. Structural and electrophysiological dysfunctions due to increased endoplasmic reticulum stress in a long-term pacing model using human induced pluripotent stem cell-derived ventricular cardiomyocytes. Stem Cell Res. Ther. 2017, 8, 109.

Statistical Method

Statistical analysis was performed using 5PSS Statistics 19.0. Normally distributed data were shown as the means (estimated by one-way analysis of variance (ANOVA)) ±standard deviation (SD) followed by the Dunnet test. Skew distributed data were expressed as the median (interquartile range), estimated by the Nemenyi test. A p-value less than 0.05 was considered statistically significant.

Example 4

Effect of BCCs on the Culture of hiPSC Cells

Two days after the start of the cell differentiation, hiPSCs grew into monolayers on 2PS, 5PS, and control surfaces. However, hiPSCs formed stereoscopic clusters on 2PM and 5PM surfaces (see FIG. 5a). hiPSC clusters were slightly larger with denser cells on the 5PM surface than on the 2PM surface. It is reported that the morphology of hiPSCs is an important factor of its pluripotency. The pluripotency of hiPSCs was confirmed by qRT-PCR on OCT4, NANOG and SOX2. The results showed that higher gene expression was found in the PM group, particularly on the 5PM surface, compared to the PS group and the control group (n=4, FIG. 5b).

Example 5

Effect of BCCs on Cardiac Differentiation of hiPSCs

Cardiac differentiation of hiPSCs was induced with small molecules (FIG. 4). Eight days after the start of the differentiation, spontaneous beating cardiomyocytes were observed on all surfaces. The morphology of hiPSC-CMs was still 2D-like cell sheets on the control and PS groups, while these formed 3D-like spheroids in PM groups.

It has been reported that MLC2v-positive result means ventricular-like cardiomyocytes, while MLC2v-positive/MLC2a-negative result means mature ventricular-like cardiomyocytes [4, 5]. In chamber-specific analysis, a similar proportion of MLC2v-positive hiPSC-CMs (about 95%) was found on all surfaces, suggesting that the majority of hiPSC-CMs were ventricular-like cardiomyocytes. However, the ratio of mature ventricular cardiomyocytes, defined as MLC2v+/MLC2a− cells, was higher on PM groups (about 80%) than on PS groups and the control (<60%), suggesting that PM surfaces promoted the pronounced maturation of hiPSC-CMs (FIG. 6). hiPSCs on PM substrates formed 3D-like spheroids which had stronger cell-cell contacts and higher pluripotency compared to those monolayer hiPSCs on PS and control surfaces. This phenomenon in turn generates functional and mature hiPSC-CMs compared to controls.

Example 6

PM Substrates Improved Cardiac Structural Maturation of hiPSC-CMs

Previous studies suggest that adult cardiomyocytes exhibit an elongated shape with organized myofibrils [6]. 30 days after the differentiation, hiPSC-CMs on different surfaces were trypsinized into single cells and replated on gelatin-coated plates. In detail, single hiPSC-CM from PM groups was more elongated, while those from PS groups and the control were less elongated (FIG. 7a). The spatial organization of myofibrils was highly ordered and clear on BCCs but not on controls. α-Actinin is parallel and anisotropic when cells were elongated, which was observed in PM-derived hiPSC-CMs.

Quantitative analyses of cell morphology including the aspect ratio, circularity, spreading area, and parameter of cells showed that the aspect ratio of 5PM-derived hiPSC-CMs was significantly higher and the circularity of PM-derived hiPSC-CMs was significantly lower compared to the controls (n=40-44, FIG. 7b and FIG. 7c).

Another mature indicator, myofibrils or the length of sarcomeres, is directly related to the contraction force of cardiomyocytes [7]. The length of sarcomeres was significantly longer on PM-derived hiPSC-CMs compared to other surfaces (FIG. 4d).

Taken together, these results indicate that PM surfaces promoted the structural maturation of hiPSC-CMs.

Example 7

PM Substrates Improved the Maturation of Electrophysiological Properties of hiPSC-CMs To verify the electrophysiological properties, the AP was analyzed using the patch-clamp method [3]. AP duration at 50% and 90% repolarization (APD50 and PAD90) was measured by the patch-clamp method. The results showed that PM surfaces prolonged APD50 and APD90 (n=10, FIG. 9b and FIG. 9c). Moreover, the ratio of APD50/APD90 was greater than 0.8 on PM surfaces, while that on the PS surfaces and control was about 0.7 (FIG. 9d). The result again suggested that PM substrates promoted hiPSC-CMs toward more mature ventricular cardiomyocytes.

qRT-PCR was performed to test the expressions of essential cardiac genes in hiPSC-CMs 30 days after the differentiation on BCCs including cardiac structural component genes (ACTC1 and TNNT2), $Ca^{2+}$ transient-related proteins (RYR2 and SERCA2a), major cardiac ion-channel genes (SCN5a, KCNJ2, and CACNA1c), cell membrane surface genes (ITGB1 responsible for information transfer between cells and extracellular matrix, and GJA1 responsible for cell-to-cell gap junction intracellular communication to regulate cell death), and myofibrillar isoforms (MYH6 and MYH7). Consistent with functional experiments, PM substrates, especially 5PM, significantly enhanced the expressions of these critical cardiac genes, which expressions were higher than the expressions of these genes in adult myocardium (n=4, FIG. 8). Notably, myosin heavy chain (MHC) isozymic transitions from MHC-α to MHC-β were known as cardiac development/maturation markers [8]. In the present example, the 5PM surface significantly increased the RNA expressions of MHC-β (MYH7), whereas the expressions of MHC-α (MYH6) did not differ among the five surfaces. Altogether, 5PM surfaces promote the maturation of hiPSC-CMs compared to PS surfaces and the 2D control.

Example 8

5PM Substrate Promoted the N-Cadherin Expression During Cardiogenesis

The BCC-induced higher cell-cell contact is crucial in cardiac differentiation of hiPSCs. This effect was verified by analyzing cadherins, cell adhesion molecules. During cardiogenesis, the expression of E-cadherin is gradually suppressed with a gradual increase of N-cadherin expression. This process is known as cadherin switching, a hallmark of epithelial-to-mesenchymal transition (EMT) [9, 10]. It has also been reported that the presence of N-cadherin at the cell surface of cardiomyocytes is necessary for the contraction [11, 12, 13]. Herein, hiPSC-CMs on PM substrates formed 3D-like spheroids, indicating an increase of cell-cell contacts.

Immunostaining showed that the expression of N-cadherin was stronger on PM surfaces than on other surfaces, while E-cadherin has similar low intensity across surfaces after 8 days (FIG. 10a).

Owing to the topography of BCC materials, it is not easy to obtain a clear picture from a specific stack. Hence, further western blot analysis was carried out. N-Cadherin expression was detected by Western blot. Consistently, it demonstrated that the 5PM surface significantly increased the expression of N-cadherin, while the expressions of E-cadherin showed no differences among all the groups (n=3, FIG. 10b and FIG. 10c).

These results indicated that PM substrates provided optimized biophysical stimulation through cell-surface and cell-cell interactions to hiPSCs which maintained the pluripotency of hiPSCs during expansion and facilitated cardiac differentiation of hiPSCs induced by small molecules.

In summary, BCCs are versatile platforms that have multidimensional structures and heterogeneous chemistries. These are important modulators in the cell microenvironment. BCCs with different combinations can be fabricated in a short period of time which can be used to screen the cell-substrate interaction. Using this high-throughput screening platform, the BCCs optimized in the modulation of the hiPSC behavior can be obtained. hiPSC expansion and cardiac differentiation can be performed on BCCs using the one-step method without EB formation. More importantly, mature and functional hiPSC-CMs can be generated on optimized BCCs, that is, 5PM surfaces. The mechanism was answered that surface properties of PM groups altered cell morphology and facilitated cell-cell contacts and cadherin switching during cardiac differentiation. Improvement of the N-cadherin expression enhanced EMT that benefited the differentiation of hiPSCs into globally mature cardiac cells. The method of the present disclosure provided a simple and efficient way to produce mature hiPSC-CMs.

p1) The method for culture and differentiation of cells the present disclosure using the membrane of the present disclosure is a one-step method. That is, the culture and differentiation of pluripotent stem cells, such as hiPSCs, are carried out on a multi-scale particle membrane. Compared with the existing 3D culture technology which is a two-step method including forming EBs first, and then transferring to the 3D scaffold for differentiation, the method of the present disclosure is time and effort saving, and reduces the chance to damage and contaminate cells. In contrast to the existing 2D culture techniques, in which trypsin digestion is required to separate cultured or differentiated cells from the substrate, the method of the present disclosure can separate cultured or differentiated cells from the membrane using a simple means such as flushing, thus simplifying the process and reducing damages to cells.

2) The membrane and cell culture method of the present disclosure may allow stem cells, such as hiPSCs, to grow in the form of 3D-like spheroids, maintaining their pluripotency and stemness.

3) Using the membrane and culture method of the present disclosure, more mature differentiated stem cells, such as hiPSC-CMs, can be obtained in the same period of time compared with the traditional methods.

What is claimed is:

1. A method for differentiation of human induced pluripotent stem cells (hiPSCs) into hiPSC-derived cardiomyocytes (hiPSC-CMs), comprising differentiating the hiPSCs on a membrane pre-coated with a solubilized basement membrane preparation comprising:

a base portion; and a protrusion array composed of a plurality of protrusions, the plurality of protrusions being substantially uniformly distributed on the base portion, and, each protrusion having a micrometer-scale dimension.

2. The method according to claim 1, further comprises detaching and collecting the cells from the membrane by liquid flushing or suction without using an enzyme.

3. The method according to claim 1, wherein a distance between adjacent protrusions is on the order of micrometers.

4. The method according to claim 1, wherein the membrane is a colloidal crystal membrane.

5. The method according to claim 1, wherein the membrane is composed of particles of different particle sizes of two or more types, and the two or more types of particles of different particle sizes comprise at least:

particles of a first type, serving as the protrusions and having an average particle size of 1 μm to 50 μm, and particles of a second type, serving as the base portion and having an average particle size less than or equal to $\frac{1}{10}$ of the average particle size of the first type of particles.

6. The method according to claim 1, wherein the membrane is composed of particles of different particle sizes of two types, wherein in the particles of different particle sizes of the two types, particles of a first type have an average particle size of 1 $\mu$m to 50 $\mu$m, and particles of a second type have an average particle size of 10-900 nm.

7. The method according to claim 6, wherein the particles of the first type are made of an inorganic compound.

8. The method according to claim 6, wherein the particles of the second type are made of an organic polymer.

9. The method according to claim 6, wherein the particles of the first type are made of one or more materials selected from the group consisting of silica, titania, zinc oxide, chemically modified silica, chemically modified titanium dioxide, chemically modified zinc oxide, and any combination thereof.

10. The method according to claim 6, wherein the particles of the second type are made of one or more materials selected from the group consisting of polystyrene, acrylic polymers, chitosan, poly(lactic-co-glycolic acid), polylactic acid, polycaprolactone, gelatin and any combination thereof.

11. The method according to claim 10, wherein the acrylic polymers are selected from the group consisting of poly (meth)acrylic acids, poly(meth)acrylates and any combination thereof.

12. The method according to claim 11, wherein the poly(meth)acrylates are selected from the group consisting of poly(meth)acrylic acid $C_1$-$C_{20}$ alkyl esters.

13. The method according to claim 11, wherein the poly(meth)acrylates comprise at least one selected from the group consisting of poly(methyl acrylate), poly(methyl methacrylate), poly(ethyl acrylate), poly(ethyl methacrylate), poly(propyl acrylate), poly(propyl methacrylate), poly (butyl acrylate), poly(butyl methacrylate), poly(pentyl acrylate), poly(pentyl methacrylate), poly(hexyl acrylate), poly (hexyl methacrylate), and any combination thereof.

14. The method according to claim 6, wherein the particles of the first type are made of silica and the particles of the second type are made of poly(methyl methacrylate).

15. The method according to claim 6, wherein the particles of the first type are in the form of a single layer of particles, and a ratio of the particles of the first type and the particles of the second type is set such that the particles of the first type are distributed in the particles of the second type in a partially embedded manner to form a colloidal crystal.

* * * * *